United States Patent
Fu et al.

(10) Patent No.: US 9,447,803 B1
(45) Date of Patent: *Sep. 20, 2016

(54) AO QUICK CONNECT INTERFACE

(71) Applicant: Holmed, LLC, Franklin, MA (US)

(72) Inventors: Rick Fu, Quincy, MA (US); Scott Foret, Allston, MA (US)

(73) Assignee: Holmed, LLC, Franklin, MA (US)

( * ) Notice: Subject to any disclaimer, the term of this patent is extended or adjusted under 35 U.S.C. 154(b) by 764 days.

This patent is subject to a terminal disclaimer.

(21) Appl. No.: 13/722,678

(22) Filed: Dec. 20, 2012

(51) Int. Cl.
*F16B 7/00* (2006.01)
*F16B 7/04* (2006.01)

(52) U.S. Cl.
CPC .................. *F16B 7/0406* (2013.01)

(58) Field of Classification Search
None
See application file for complete search history.

(56) References Cited

U.S. PATENT DOCUMENTS

| | | | |
|---|---|---|---|
| 3,583,715 A * | 6/1971 | Jahrl | B23B 31/1071 279/75 |
| 4,692,073 A * | 9/1987 | Martindell | B23B 31/1071 279/75 |
| 5,271,697 A * | 12/1993 | Johnson | B23B 31/1071 279/75 |
| 5,624,214 A * | 4/1997 | Carroll | B23Q 1/703 279/105.1 |
| 6,457,916 B2 | 10/2002 | Wienhold | |
| 7,175,185 B2 | 2/2007 | Chen | |
| 7,296,804 B2 * | 11/2007 | Lechot | A61B 17/1666 279/140 |
| 7,448,302 B2 | 11/2008 | Huang | |
| 7,469,909 B2 | 12/2008 | Strauch et al. | |
| 7,565,854 B2 | 7/2009 | Chiang et al. | |
| 7,581,470 B1 | 9/2009 | Huang | |
| 7,669,860 B2 | 3/2010 | Chiang | |
| 7,740,249 B1 | 6/2010 | Gao | |
| 7,922,180 B2 | 4/2011 | Meng | |
| 7,922,720 B2 * | 4/2011 | May | A61B 17/32002 606/79 |
| 2004/0220554 A1 * | 11/2004 | Lechot | A61B 17/1666 606/1 |
| 2005/0036844 A1 | 2/2005 | Hirt et al. | |
| 2005/0176283 A1 | 8/2005 | Cantlon | |

OTHER PUBLICATIONS

U.S. Patent Application Serial No.: Not Yet Assigned, Filed: Dec. 20, 2012 by Rick Fu et al. for a Improved Square Quick Connect Interface, pp. 1-24.

\* cited by examiner

*Primary Examiner* — Victor MacArthur
(74) *Attorney, Agent, or Firm* — Cesari and McKenna, LLP; James A. Blanchette

(57) ABSTRACT

In one embodiment, a quick connect interface for a surgical instrument includes a body having an inner cavity that includes a flat. Two or more ball bearings are each disposed in a respective hole in the body. A sleeve is slideable along the body. The sleeve includes a camming ramp that urges the two one or more ball bearings to partially extend through the holes into the inner cavity when the sleeve is in a locked position. The two or more ball bearings are positioned to, when the shaft of the replaceable tool is disposed in the inner cavity, urge the shaft to a side of the inner cavity that includes the flat. The ball bearings may be positioned radially about a central axis of the body substantially 90 degrees apart. The camming ramp may include at least one plateau that prevents unintentional release of the shaft.

20 Claims, 6 Drawing Sheets

AO QUICK CONNECT INTERFACE

BACKGROUND

1. Technical Field

The present disclosure relates generally to surgical instruments, and more specifically to quick connect interfaces used to connect a shaft of a replaceable tool to a drive mechanism.

2. Background Information

Quick connect interfaces (or simply "quick connects") are widely used in surgical instruments to connect a shaft of a replaceable tool, such as a bit, to a drive mechanism, such as a ratcheting or non-ratcheting handle or a motor-operated drive. These surgical instruments may be used to perform a variety of surgical tasks, including drilling, reaming, tapping, placement of bone screws, assembly of spinal constructs, and the like. One common type of quick connect interface that may be employed is an Association for Osteosynthesis (AO)-style quick connect interface, typically referred to simply as an "AO quick connect interface". Such an interface may be used with a wide variety of different types of replaceable tools, as well as different drive mechanisms.

A typical AO quick connect interface is configured to receive an end of a shaft having a D-shaped profile. A flat portion defined by the D-shaped profile of engages another flat portion (referred to herein as the "AO flat") formed in an inner cavity of the AO quick connect interface. This engagement prevents rotation of the shaft with respect to the interface. The shaft may be retained in the interface by the operation of ball bearings. Two ball bearings are generally positioned radially about a central axis of the interface, about 180 degrees apart. The ball bearings may engage a groove formed in the end of the shaft. The ball bearings are often held by a substantially straight walled portion of the sleeve.

While such an arrangement may prevent removal of a replaceable tool, it may not hold the tool very securely. There is often substantial axial and lateral play. There may be minor variations in the shaft of replaceable tools, such that diameters of the groove may vary from one replaceable tool to the next. However, ball bearings positioned radially about 180 degrees apart, and held by straight walled portions, cannot effectively adapt to such variation. This may results in each replaceable tool fitting differently. In some cases, the fit may result in excessive amounts of play, such that the surgical instrument has a generally "sloppy" feel. This feel may be unsettling to a surgeon trying to perform a delicate surgical procedure.

Further, such an arrangement may be costly to manufacture to precise tolerances. To maintain the body of the interface as a single component, and avoid openings that would compromise function, one typically must access the region where the AO flat is to be formed through the inner cavity. With many designs, this requires the use of wire-electrical discharge-machining (wire-EDM) in the manufacturing process. While wire-EDM is capable of this type of work to very precise tolerances, it is generally a costly process, and therefore may not be suitable for low-cost instruments. Previous attempts to avoid the use of wire-EDM have generally involved multi-piece bodies that have introduced other issues, for example, have introduced unwanted play.

Accordingly, there is a need for an improved quick connect interface.

SUMMARY

In one embodiment, an improved quick connect interface (e.g., an improved AO quick connect interface) includes first and second ball bearings positioned in holes in a body, at locations substantially 90 degrees apart radially about a central axis. The holes may be positioned opposite the AO flat, such that a line segment, extending radially through a midpoint between the ball bearings and the central axis, is perpendicular to the AO flat. A spring-loaded sliding sleeve may surround a portion of the body and slide from an unlocked position to a locked position. The sleeve may be retained by a spiral retaining ring. As the sleeve is slide from the unlocked position to the locked position, the ball bearings are urged by a camming ramp formed in the sleeve into the holes, so that they partially extend through the holes into an inner cavity of the body. When so urged, they may engage a groove formed in an end of the shaft of a replaceable tool disposed therein. The pressure applied by the ball bearings may urge the shaft of the replaceable tool towards the side of the inner cavity of the body that includes the AO flat. Such urging may ensure firm contact between the flat portion of the shaft, and the AO flat of the inner cavity of the interface. The effect of the urging may serve to accommodate any minor variations in the shaft and groove, and reduce both lateral and axial play.

The camming ramp may be formed with a special double-plateau profile, where the generally angular profile of the camming ramp is interrupted by first and second substantially-flat plateaus oriented substantially parallel to the central axis. The first plateau may be disposed at the top of the ramp and operate to receive the ball bearings when the sleeve is in the unlocked position. The second plateau may be disposed proximate the bottom of the ramp, near the location of the ball bearings when the sleeve is in the locked position, and serve to prevent unintentional releases of the shaft. While the second plateau may be near the ball bearings when the sleeve is in the locked position, the ball bearings may still contact a generally angular portions of the camming ramp absent external forces.

A slot may extend through the body radially with the midpoint between the two ball bearings. The slot extends into the inner cavity and has a flat bottom that constitutes the AO flat. Due to the arrangement of the first and second ball bearings, and their urging of the shaft towards the side of the inner cavity that includes the AO flat, and thereby away from the opening created by the shaft, the presence of the opening may not compromise stability. The slot, and thereby the AO flat, may be milled into the body using inexpensive milling processes, absent the use of wire-EDM.

BRIEF DESCRIPTION OF THE DRAWINGS

The detailed description below refers to the accompanying drawings of example embodiments.

DETAILED DESCRIPTION OF EXAMPLE EMBODIMENTS

Figure 1:
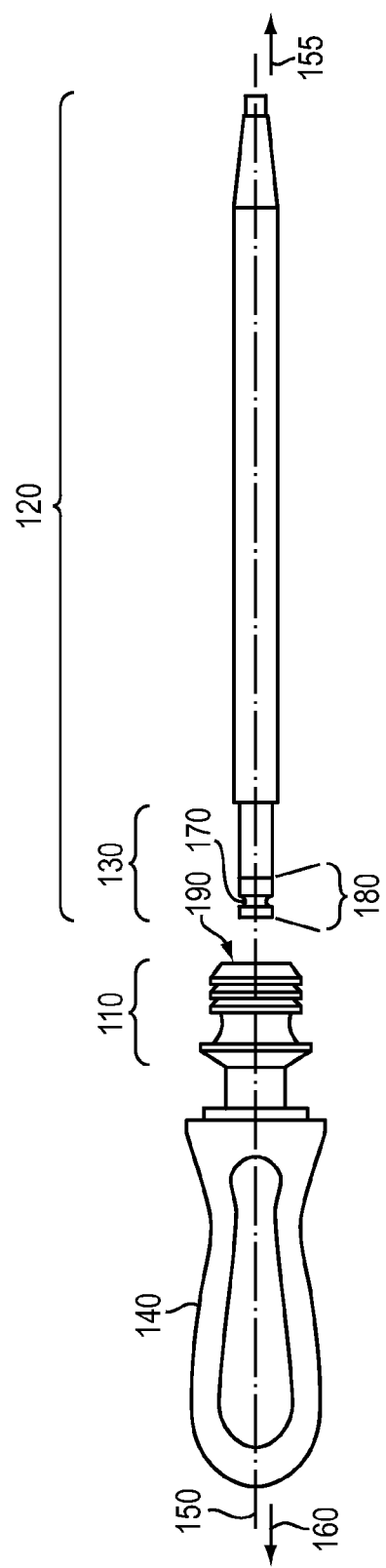
FIG. 1 is a perspective view of an example surgical instrument that includes an example improved quick connect interface (in this example, an improved AO quick connect interface) and an example replaceable tool (in this example, a hex bit having a shaft with an end having a D-shaped profile)

Referring to FIG. 1, an example surgical instrument 100 may include an example improved quick connect interface 110 (in this example, an improved AO quick connect interface), and an example replaceable tool 120 (in this example, a hex bit). A drive mechanism 140 is coupled to the improved quick connect interface 110. In this example, the drive mechanism 140 is a non-ratcheting molded handle. Alternatively, other drive mechanisms may be used, including ratcheting and non-ratcheting handles or a motor-operated drive. A central axis 150 may extend through the center of the surgical instrument 100, and in turn the quick connect interface 110. The central axis may extend in both a distal direction 155, and a proximal direction 160.

Figure 2A:
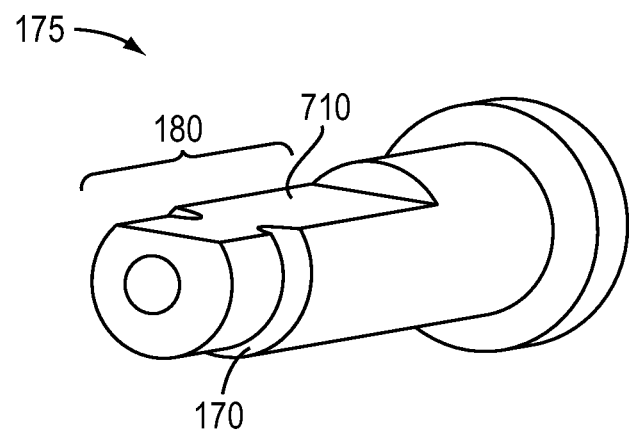
FIG. 2A is a perspective view of an example end of the shaft.
Figure 2B:
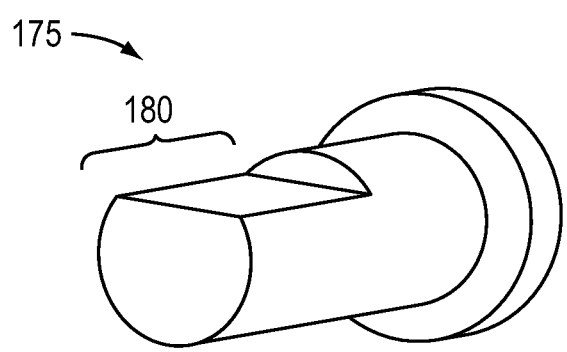
FIG. 2B is a cut-away perspective view of the example end of the shaft, showing, among other things, the D-shaped profile.

Referring to FIGS. 1-2B, a generally-cylindrical shaft 130 of the replaceable tool 120 may include an end 180 having a D-shaped profile (i.e. cross section), which defines a flat portion 210. A semi-circular groove 170 may be formed in the end 180. The shaft 130, including the end 180, may be inserted by movement in the proximal direction 160 into an inner cavity 190 of the quick connect interface 110, and secured therein.

Referring to FIGS. 3-5B, the example improved quick connect interface 110 includes a generally cylindrical body 310 into which the inner cavity 190 may be formed. The body 310 may have an inner surface that defines the inner cavity 190, and is shaped to accommodate the shaft 130, and its end 180. The inner cavity 190 may be formed to have a flat portion (referred to herein as the "AO flat") 305 that may engage the flat portion 210 of the end 180 of the shaft 130. The engagement of the flat portion 210 with the AO flat 305 prevents rotation of the replaceable tool 120 with respect to the interface 110.

A first and a second ball bearing 320 may be positioned in holes 325 in the body 310, which extend from the outer surface to the inner surface. The holes 325 may be sized to permit the ball bearings 320 to extend into the inner cavity 190, but not pass completely therethrough. Each set of holes 325 and ball bearings 320 may be positioned substantially 90 degrees apart from the other, radially about the central axis 150. The holes 325 may be positioned opposite the AO flat 305, such that a line segment 510 extending through a midpoint between the ball bearings and the central axis 150 is perpendicular to the AO flat 310.

A sliding sleeve 315 may surround a portion of the body 310, the first and second ball bearings 320, and other components of the quick connect interface 110. The sleeve 315 may be retained on the body 310 with a spiral retaining ring 330. Retaining the sleeve with a spiral retaining ring may simplify manufacture, obviating a need to roll form the sleeve onto the body.

The sleeve 315 slides from an unlocked position (FIG. 3), where the sleeve is shifted towards a proximal end of the interface 110, to a locked position (FIG. 4), where the sleeve 315 is shifted towards a distal end of the interface 110. A compression spring 335 may surround a portion of the body 310, and may urge the sleeve 315 in the distal direction 155, so that, when at rest, the sleeve 315 is in the locked position. One end of the compression spring 335 may engage a lip 345 formed in the sleeve 315, while the other end may engage a portion of the body 310. A finger ledge 340 may be formed in the sleeve 315, so that one may pull the sleeve in the proximal direction 160, to the unlocked position, against the resistance of the compression spring 335.

Figure 3:
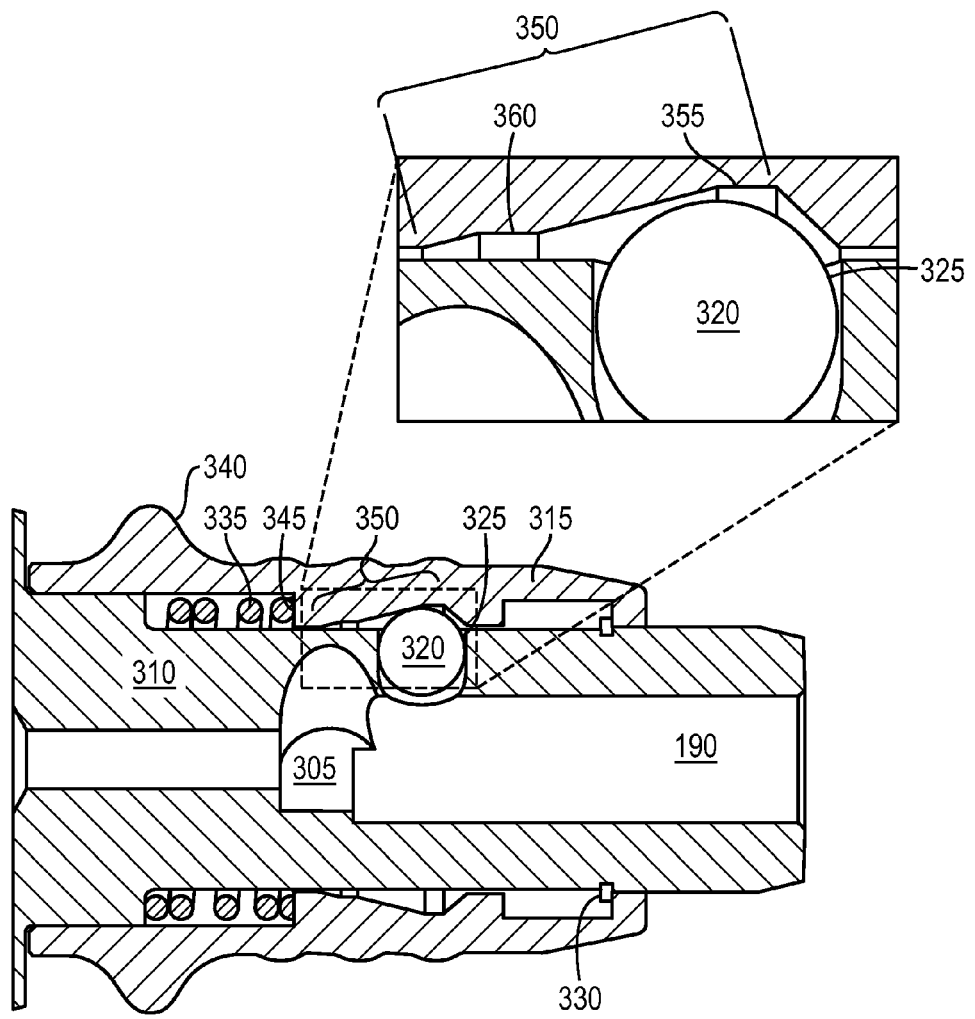
FIG. 3 is a cut-away side view, with an enlargement, of the example improved quick connect interface showing, among other things, ball bearings when the sliding sleeve is in an unlocked position.
Figure 4:
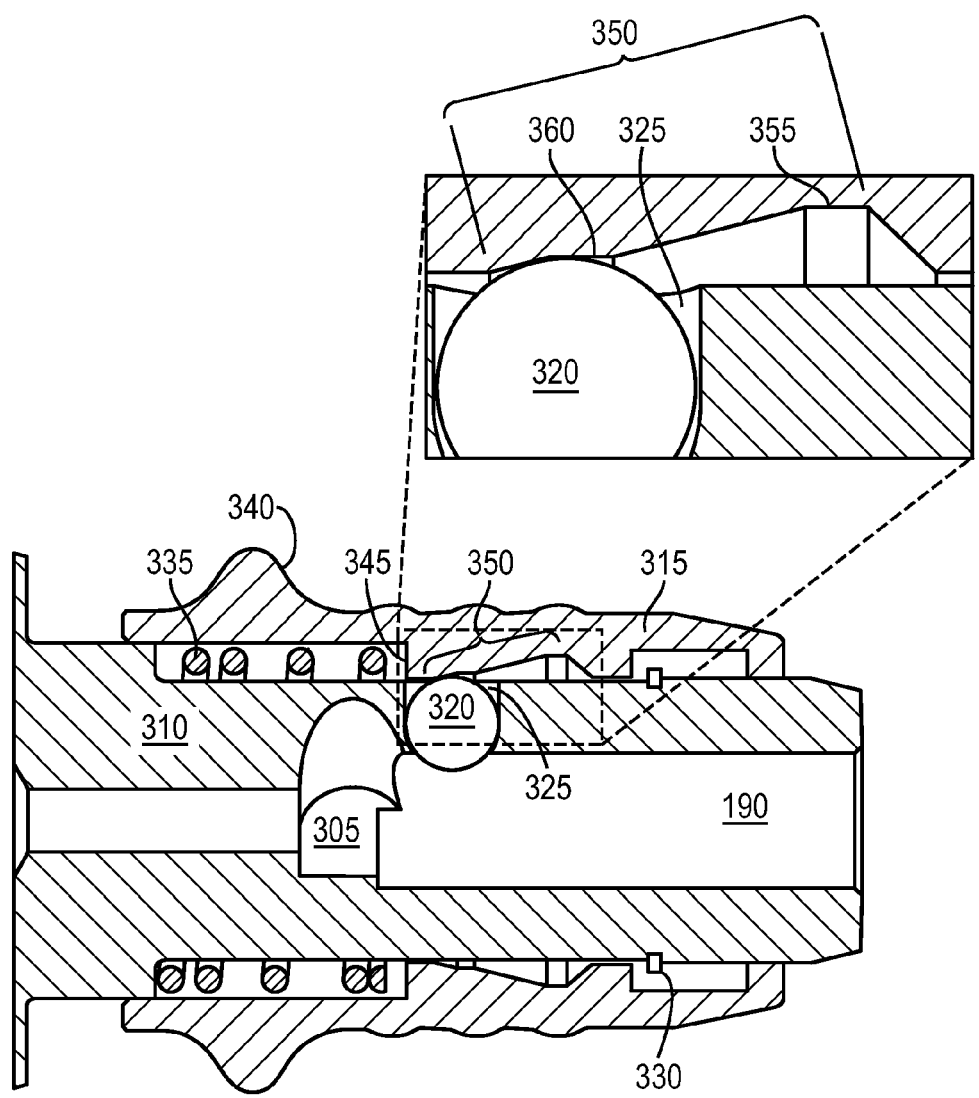
FIG. 4 is a cut-away side view, with an enlargement, of the example improved quick connect interface showing, among other things, ball bearings when the sliding sleeve is in a locked position.
Figure 5A:
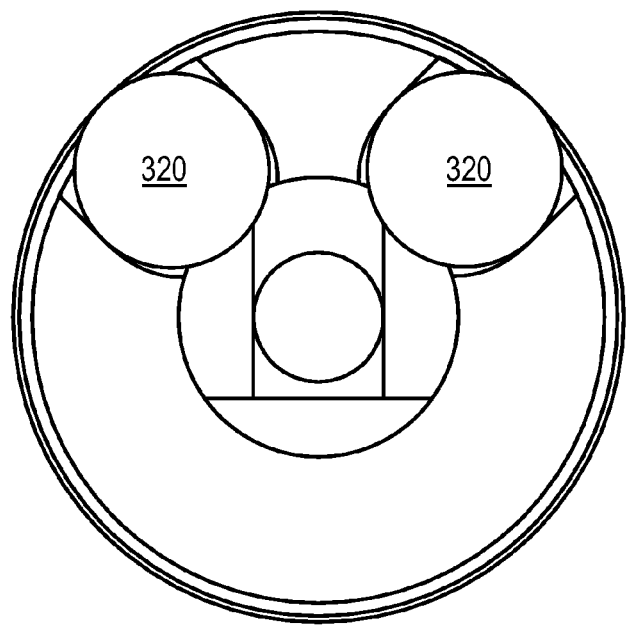
FIG. 5A is an front view of the example improved quick connect interface showing, among other things, the positioning of the ball bearings.
Figure 5B:
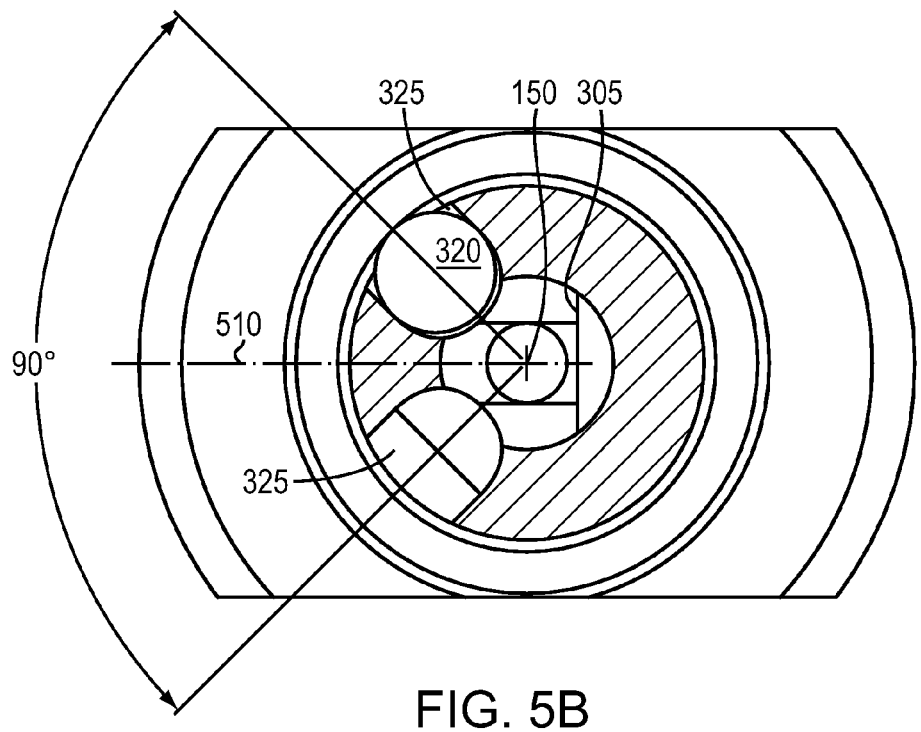
FIG. 5B is a front cross section of the example improved quick connect interface showing, among other things, one ball bearing removed to show the hole that accommodates it.

Referring to FIGS. 3-4, a camming ramp 350 may be formed in an interior surface of the sleeve 315, proximate the ball bearings 320. As the sleeve 315 is slide from the unlocked position (FIG. 3) to the locked position (FIG. 4), the ball bearings 320 may be urged by contact with the camming ramp 350 into the holes 325, so that they partially extend through the holes into the inner cavity 190. When so urged, they may engage the groove 170 formed in the end 180 of the shaft 130 of the replaceable tool 120. The camming ramp 350, in conjunction with the compression spring 335, may cause the ball bearings 320 to apply pressure to the groove 170 when the sliding sleeve is in the locked position. Since the ball bearings are positioned substantially 90 degrees apart radially about the central axis 150, opposite the AO flat 305, the pressure applied by the ball bearings, may urge the shaft 130 towards the side of the inner cavity 190 that includes the AO flat 305. Such urging may ensure firm contact between the flat portion 210 defined by the D-shaped profile of the end 180 of the shaft 170, and the AO flat 305. The overall effect of the urging may accommodate any minor variations in the shaft, and reduce both lateral and axial play.

When the sleeve 315 is returned to the unlocked position (FIG. 3), pressure on the ball bearings 220 from the camming ramp 310 may be removed. The ball bearings 320 are allowed to recess in their holes 325 from the inner cavity 190. The shaft 130 of the replaceable tool 120 may then be removed from the quick connect interface 110.

The camming ramp 350 may be formed with a special double-plateau profile, where the generally angular profile of the camming ramp is interrupted by first and second substantially-flat plateaus 355, 360, which are oriented substantially parallel to the central axis 150. The second of the substantially-flat plateaus 360 may act to prevent unintentional release of the shaft 130 of the replaceable tool 120. Unintentional release could occur if sufficient force were exerted upon the replaceable tool 120 in the distal direction 155. This force would be transmitted by the shaft 130, to the ball bearings 320, which in turn would transmit it to the camming ramp 350 and the sleeve 315. If the force upon the sleeve 315 exceeds the force exerted by the compression spring 335 that maintains the sleeve in the locked position, the sleeve will retract, and the shaft 130 will be unintentionally released.

The first plateau 355 may be disposed at the top of the ramp and operate to receive the ball bearings 320 when the sleeve 315 is in the unlocked position. The second plateau 360 may be disposed proximate to the bottom of the ramp, near the location of the ball bearings when the sleeve 315 is in the locked position (FIG. 4). While the second plateau 360 may be near the ball bearings 320 when the sleeve is in the locked position, the ball bearings may still contact a generally angular portion of the camming ramp 350, absent external forces. This may ensure the above discussed urging of the shaft 130 to one side. Should force be exerted in the distal direction 155 upon the replaceable tool 130, and the ball bearings 220 begin to move up the camming ramp 310, their travel will be interrupted by the second plateau 355. When they encounter the second plateau 360, due to the lack of angle, the ball bearings 320 will no longer be able to exert force onto the camming ramp 350 in a direction parallel to the central axis 150, and thereby will not cause the sleeve 315 to retract. In this manner, unintentional release is prevented.

Figure 6A:
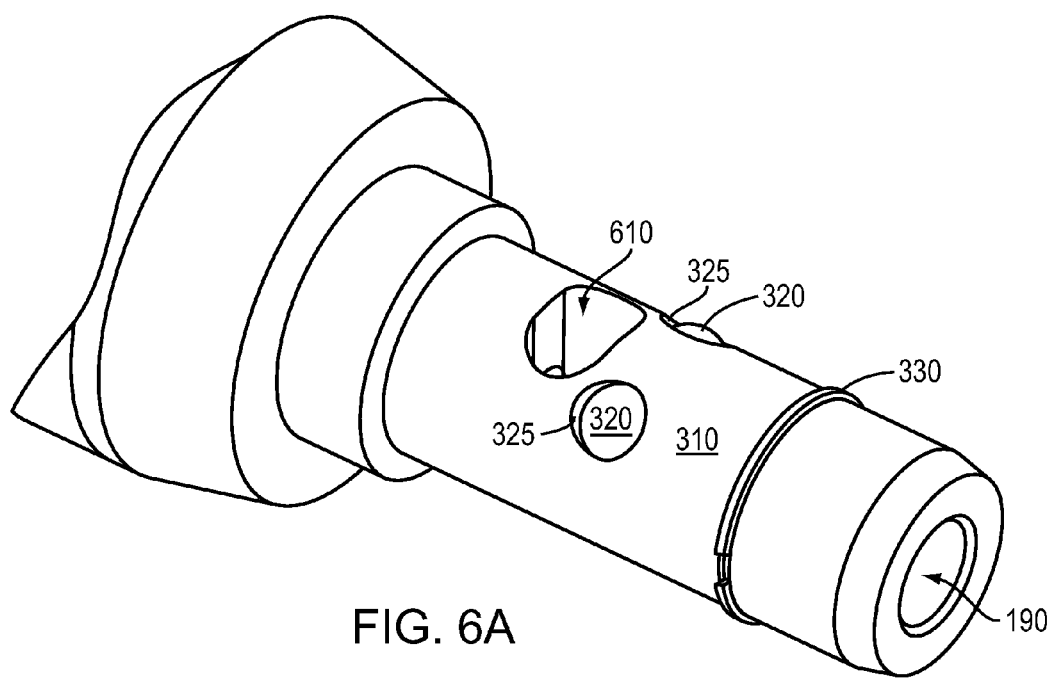
FIG. 6A is an enlarged perspective view of a portion of the example surgical instrument showing the example improved quick connect interface with the sleeve removed, and illustrating a slot that extends through the body.
Figure 6B:
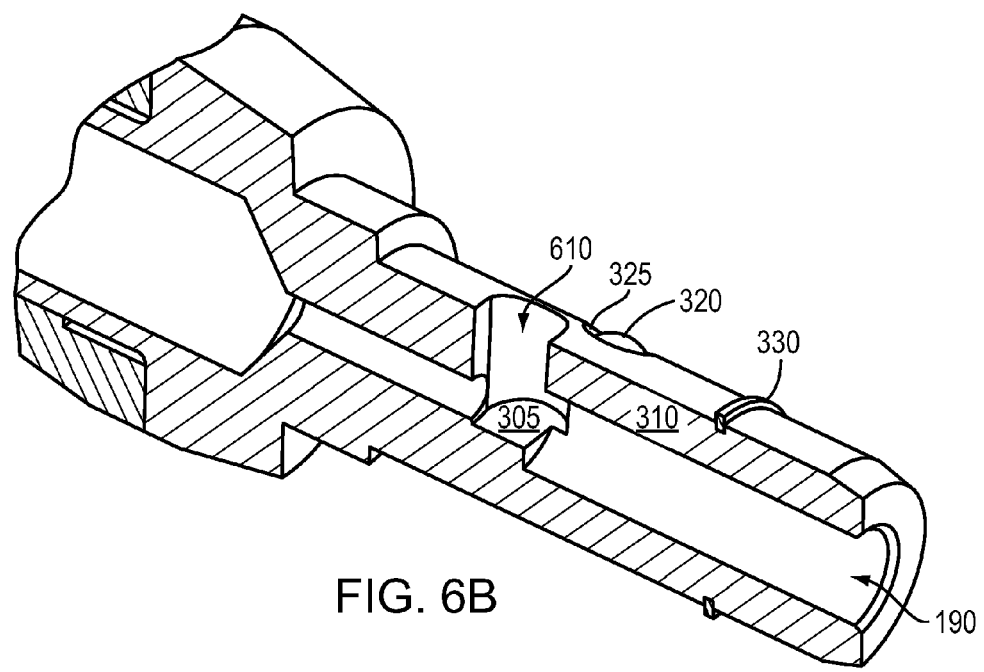
FIG. 6B is an enlarged perspective cross section of the portion of the example surgical instrument shown in FIG. 6A, further illustrating the slot that extends through the body.

Referring to FIGS. 6A and 6B, a slot 610 may extend through the body 310, from the outer surface into the inner cavity 190. In one implementation, the slot may be radially aligned about the central axis with the midpoint between the two ball bearings 320. A flat bottom of the slot 610 constitutes the AO flat 305. Due to the arrangement of the first and second ball bearings 320, and their urging of the shaft towards the side of the inner cavity of the body that includes the AO flat 320, and thereby away from the opening created by the shaft 610, the presence of the opening may not compromise stability. Pressure is already absent in the region where the material is removed.

Since it is readily accessible from the exterior of the body 310, the shaft 610, and thereby the AO flat 305, may be milled into a single-piece body using inexpensive milling processes. Potentially costly wire-EDM, or use of a multi-piece body, may not be need, at least in this embodiment.

While the above description discusses at least one example embodiment of the improved quick connect interface, it should be apparent that a number of other embodiments may be implemented. Such embodiments may include a wide variety of modification and/or additions to what is described above, to embrace this disclosure's intended spirit and scope.

It is discussed above that the quick connect interface 110 may be an AO quick connect interface. It should be understood that the techniques may be readily adapted to work with pull or push variants of this type of interface. It should also be understood that at least some of the techniques may be readily adapted to work with other types of interfaces, for example, ¼ square, Zimmer, Hudson or other types of interfaces.

Similarly, while it is discussed above that two ball bearings are used, it should be understood that a different number of bearings may be used in other embodiments. For example, a single bearing may be employed, or three bearings may be used. Such bearings need not be ball bearings. One or more other types of bearings, for example, cylindrical roller bearings, may be readily substituted for the ball bearings discussed above.

Further, while it is discussed above that a compression spring is used, it should be understood that other means may be used for urging the sleeve to a locked position. For example, one or more tension springs may be employed.

Further, while it is discussed above that a camming ramp is used, it should be understood that other means may be used for urging ball bearings to partially extend through the holes into the inner cavity when the sleeve is in the locked position. For example, one or more springs could be employed.

Further, while certain approximate angles are discussed above, a variety of other angles may alternatively be employed, depending on the particular implementation. As used herein, when an angle is stated to be "substantially" of a certain degree measure, it should be understood that measures of up to plus or minus 10 degrees of the stated angle are to be considered substantially of that degree measure.

Further, it should be understood that a quick connect interface may be constructed from a variety of materials, including stainless steel, aluminum, other metals, plastics, and combinations thereof.

In general, it should be understood that the above descriptions are meant to be taken only by way of example.

What is claimed is:

1. A quick connect interface for a surgical instrument, comprising:
    a body having an outer surface, and having an inner surface that defines an inner cavity, the inner cavity shaped to accommodate a generally-cylindrical shaft of a replaceable tool, the inner cavity having a flat portion shaped to engage another flat portion formed by a profile of an end of the shaft;
    two or more ball bearings positioned radially about a central axis of the body, each ball bearing disposed in a respective hole in the body that extends from the outer surface to the inner surface of the body, wherein there are no ball bearings positioned radially about the central axis opposing the two or more ball bearings; and
    a sleeve that surrounds a portion of the body and is slideable along the body, from an unlocked position to a locked position, the sleeve including a camming ramp that contacts the two or more ball bearings, the camming ramp arranged to urge the two or more ball bearings to partially extend through the holes into the inner cavity when the sleeve is in the locked position,
    wherein the two or more ball bearings are positioned to, when the shaft of the replaceable tool is disposed in the inner cavity, urge the shaft more to a side of the inner cavity that includes the flat portion than an opposing side of the inner cavity.

2. The quick connect interface of claim 1, wherein the two or more ball bearings comprise first and second ball bearings positioned radially about a central axis of the body, substantially 90 degrees apart.

3. The quick connect interface of claim 1, wherein the camming ramp includes at least one plateau that is oriented substantially parallel to a central axis of the body and interrupts an angle of the camming ramp, the at least one plateau positioned to prevent unintentional release of the shaft of the replaceable tool should force be exerted upon the replaceable tool in a distal direction while the sleeve is in the locked position.

4. The quick connect interface of claim 3, wherein the at least one plateau comprises a first plateau and a second plateau, the first plateau positioned to receive the two or more ball bearings when the sleeve is in the unlocked position, and the second plateau positioned to prevent unintentional release of the shaft of the replaceable tool should force be exerted upon the replaceable tool in the distal direction while the sleeve is in the locked position.

5. The quick connect interface of claim 1, wherein the body includes a slot that extends from the outer surface into the inner cavity, the slot having a flat bottom that constitutes the flat portion of the inner cavity.

6. The quick connect interface of claim 5, wherein the two or more ball bearings comprise first and second ball bearings, and the slot is radially aligned about a central axis of the body with the midpoint between the first and second ball bearings.

7. The quick connect interface of claim 1, further comprising
a spiral retaining ring disposed about the body that retains the sleeve upon the portion of the body.

8. The quick connect interface of claim 1, wherein the quick connect interface is an AO quick connect interface.

9. A surgical instrument that includes a quick connect interface, comprising:
a drive mechanism;
a replaceable tool having a shaft, an end of the shaft having a flat portion formed by a profile of the end; and
a quick connect interface coupled to the drive mechanism, and configured to connect to the shaft of the replaceable tool, the quick connect interface including:
a body having an outer surface, and having an inner surface which defines an inner cavity that is shaped to accommodate the shaft of the replaceable tool, the inner cavity having a flat portion shaped to engage another flat portion formed by a profile of an end of the shaft,
two or more ball bearings positioned radially about a central axis of the body, each ball bearing disposed in a respective hole in the body that extends from the outer surface to the inner surface of the body, wherein there are no ball bearings positioned radially about the central axis opposing the two or more ball bearings,
a sleeve that surrounds a portion of the body and is slideable along the body, from an unlocked position to a locked position, the sleeve including a camming ramp that contacts the two or more ball bearings, the camming ramp arranged to urge the two or more ball bearings to partially extend through the holes into the inner cavity when the sleeve is in the locked position,
wherein the two or more ball bearings are positioned to, when the shaft of the replaceable tool is disposed in the inner cavity, urge the shaft more to a side of the inner cavity that includes the flat portion than an opposing side of the inner cavity.

10. The surgical instrument of claim 9, wherein the two or more ball bearings comprise first and second ball bearings positioned radially about a central axis of the body substantially 90 degrees apart.

11. The surgical instrument of claim 10, wherein the camming ramp includes at least one plateau that is oriented substantially parallel to a central axis of the body and interrupts an angle of the camming ramp, the at least one plateau positioned to prevent unintentional release of the shaft of the replaceable tool should force be exerted upon the replaceable tool in a distal direction while the sleeve is in the locked position.

12. The surgical instrument of claim 11, wherein the at least one plateau comprises a first plateau and a second plateau, the first plateau positioned to receive the two or more ball bearings when the sleeve is in the unlocked position, the second plateau positioned to prevent unintentional release of the shaft of the replaceable tool should force be exerted upon the replaceable tool in the distal direction while the sleeve is in the locked position.

13. The surgical instrument of claim 9, wherein the body includes a slot that extends from the outer surface into the inner cavity, the slot having a flat bottom that constitutes the flat portion of the inner cavity.

14. The surgical instrument of claim 13, wherein the two or more ball bearings comprise first and second ball bearings, and the slot is radially aligned about a central axis of the body with the midpoint between the first and second ball bearings.

15. The surgical instrument of claim 9, wherein the quick connect interface further comprises a spiral retaining ring disposed about the body that retains the sleeve upon the portion of the body.

16. The surgical instrument of claim 9, wherein the quick connect interface is an AO quick connect interface.

17. A quick connect interface for a surgical instrument, comprising:
an inner cavity sized to accommodate a shaft of a replaceable tool, the inner cavity having a flat portion shaped to engage another flat portion formed by a profile of an end of the shaft;
two or more bearings that are each disposed in a respective hole;
a sleeve that is slideable from an unlocked position to a locked position;
means for urging the two or more bearings to partially extend through the holes into the inner cavity when the sleeve is in the locked position,
wherein the two or more bearings are positioned radially about a central axis of the body substantially 90 degrees apart, wherein there are no ball bearings positioned radially about the central axis opposing the two or more ball bearings, and the two or more ball bearings are arranged to, when the shaft of the replaceable tool is disposed in the inner cavity, urge the shaft more to a side of the inner cavity that includes the flat portion than an opposing side of the inner cavity.

18. The quick connect interface of claim 17, wherein the means for urging comprises a camming ramp having at least one plateau that is oriented substantially parallel to a central axis of the body and interrupts an angle of the camming ramp, the at least one plateau positioned to prevent unintentional release of the shaft of the replaceable tool should force be exerted upon the replaceable tool in a distal direction while the sleeve is in the locked position.

19. The quick connect interface of claim 17, wherein the body includes a slot that extends from the outer surface into the inner cavity, the slot having a flat bottom that constitutes the flat portion of the inner cavity.

20. The quick connect interface of claim 17, wherein the quick connect interface is an AO quick connect interface.

\* \* \* \* \*